(12) United States Patent
Vlasenko et al.

(10) Patent No.: US 11,376,200 B2
(45) Date of Patent: Jul. 5, 2022

(54) METHODS AND KITS FOR USING BLOCKED 2-AA FOR GLYCAN ANALYSIS

(71) Applicant: Agilent Technologies, Inc., Santa Clara, CA (US)

(72) Inventors: Sergey Vlasenko, Davis, CA (US); Francis T. Haxo, San Francisco, CA (US); Andres Guerrero Navarro, Pamplona (ES)

(*) Notice: Subject to any disclaimer, the term of this patent is extended or adjusted under 35 U.S.C. 154(b) by 180 days.

(21) Appl. No.: 16/965,915

(22) PCT Filed: Jan. 31, 2019

(86) PCT No.: PCT/US2019/016169
§ 371 (c)(1),
(2) Date: Jul. 29, 2020

(87) PCT Pub. No.: WO2019/152724
PCT Pub. Date: Aug. 8, 2019

(65) Prior Publication Data
US 2021/0045981 A1   Feb. 18, 2021

Related U.S. Application Data

(60) Provisional application No. 62/625,846, filed on Feb. 2, 2018.

(51) Int. Cl.
| | |
|---|---|
| *A61K 8/36* | (2006.01) |
| *A61K 31/196* | (2006.01) |
| *G01N 33/50* | (2006.01) |
| *G01N 21/64* | (2006.01) |
| *C07C 63/06* | (2006.01) |
| *C08B 37/00* | (2006.01) |

(52) U.S. Cl.
CPC .............. *A61K 8/36* (2013.01); *A61K 31/196* (2013.01); *G01N 33/50* (2013.01); *C07C 63/06* (2013.01); *C08B 37/00* (2013.01); *G01N 21/64* (2013.01)

(58) Field of Classification Search
CPC .. A61K 31/196; A61K 31/437; A61K 31/444; A61K 31/5377; A61K 8/36; G01N 21/64; G01N 33/50; C07C 63/06; C07B 2200/05; C08B 37/00
See application file for complete search history.

(56) References Cited

U.S. PATENT DOCUMENTS

| | | | |
|---|---|---|---|
| 5,977,074 A | 11/1999 | Cordell | |
| 8,629,186 B2 | 1/2014 | Sill et al. | |
| 2004/0248890 A1 | 12/2004 | Gonzalez, III | |
| 2008/0207487 A1 | 8/2008 | DeFrees | |

OTHER PUBLICATIONS

Reiding, KR et al., High-Throughput Profiling of Protein N-Glycosylation by MALDITOF-MS Employing Linkage-Specific Sialic . . . , Anal Chem, May 2014, pp. 5784-5793, vol. 86.
Ludger, LudgerTag™ 2-AB (2-Aminobezamide) Glycan Labeling Kit, 2002 (online), [retrieved on Mar. 18, 2019], Retrieved from the internet<URL: http://search.cosmobio.co.jp/cosmo_s.
Thomas, Shane, International Search Report, PCT/US2019/0161169, dated Apr. 15, 2019.
Thomas, Shane, Written Opinion of the International Searching Authority, PCT/US2019/016169, dated Apr. 15, 2019.

*Primary Examiner* — Jennifer Wecker
*Assistant Examiner* — Kathryn Elizabeth Limbaugh
(74) *Attorney, Agent, or Firm* — Laurence J. Hyman; Hyman IP Law

(57) ABSTRACT

The present disclosure provides methods for using anthranilic acid (2-AA) blocked by tertbutyloxycarbonyl (Boc) groups in protocols for labeling glycans for analysis, and kits providing 2-AA-Boc and acids for unblocking blocked 2-AA for use in glycan labeling and analysis.

33 Claims, No Drawings

METHODS AND KITS FOR USING BLOCKED 2-AA FOR GLYCAN ANALYSIS

CROSS-REFERENCE TO RELATED APPLICATIONS

This is a national stage application under 35 U.S.C. § 371 of International Application No. PCT/US2019/016169, filed Jan. 31, 2019, which is hereby incorporated by reference for all purposes. This application further claims priority to, and the benefit of, U.S. Provisional Patent Application No. 62/625,846, filed Feb. 2, 2018, the contents of which are incorporated herein by reference for all purposes.

STATEMENT OF FEDERAL FUNDING

Not applicable.

BACKGROUND OF THE INVENTION

Determining the glycan profiles of biological samples has become important in a number of contexts. For example, determining the glycan profiles of glycoproteins such as antibody therapeutics is required to ensure consistent biological properties. Further, the glycosylation profiles need to be monitored during production of such therapeutics to protect against changes in fermentation conditions that might adversely affect the yield or properties of the agent.

A variety of labels have been developed that allow glycans attached to the label to be detected by analysis, such as by observing fluorescence of the labeled glycans or subjecting the labeled glycans to mass spectrometry. N-glycans present on glycoproteins are frequently analyzed by releasing the N-glycans from the glycoproteins with the enzyme PNGase F, and labeling the resulting glycosylamines with reagents such as those taught in co-owned U.S. Pat. Nos. 8,124,792 and 8,445,292. Another means for labeling glycans is to subject them to reductive amination with the fluorescent dyes 2-aminobenzamide ("2-AB") or anthranilic acid ("2-AA"). See, e.g., Bigge et al., "Nonselective and Efficient Fluorescent Labeling of Glycans Using 2-Amino Benzamide and Anthranilic Acid," Anal. Biochem. 230:229-238 (1995). Typically, the labeled glycans are then separated by, for example, high performance liquid chromatography ("HPLC") or capillary electrophoresis and then subjected to an analytical means, such as a fluorescence detector.

While 2-AB remains widely used for labeling glycans by reductive amination, use of 2-AA for these purposes has been made somewhat more difficult, at least in the United States, due to restrictions imposed by the Controlled Substances Act. 21 U.S.C. §§ 801 et seq. Anthranilic acid, its esters, and its salts are listed in section 802(34) of the Act as a "list 1 chemical" which is used in the manufacturing of a controlled substance. List 1 chemicals are subject to a variety of requirements regarding recordkeeping, distribution, and shipping. 2-AA is considered slightly more sensitive at labeling glycans than is 2-AB. It would be desirable if there was a convenient way to provide 2-AA in a form suitable for glycan analysis but in compliance with Drug Enforcement Administration ("DEA") rules regarding anthranilic acid, its esters, and its salts.

There remains a need for methods and kits that make 2-AA available for the reductive amination and labeling of glycans, while remaining in compliance with DEA regulations that control the distribution and shipping of 2-AA, its esters, and its salts. Surprisingly, the present invention is believed to meet these and other needs.

SUMMARY OF THE INVENTION

In some embodiments, the invention provides methods for labeling a glycan with anthranilic acid ("2-AA"). In some embodiments, the method comprises obtaining 2-AA conjugated to a tert-butyloxycarbonyl ("Boc") group ("2-AA-Boc"), removing the Boc group by incubating the 2-AA-Boc with an acid for a time and at a temperature sufficient to remove the Boc group from the 2-AA-Boc, thereby obtaining 2-AA, and incubating a solution containing the 2-AA and the glycan under conditions that allow the 2-AA to label the glycan, thereby labeling the glycan with 2-AA. In some embodiments, the acid is trifluoroacetic acid, difluoroacetic acid, or hydrochloric acid. In some embodiments, the acid is difluoroacetic acid ("DFA"). In some embodiments, the temperature sufficient to remove said Boc group from the 2-AA-Boc is 50-90° C. In some embodiments, the temperature sufficient to remove the Boc group from the 2-AA-Boc is about 70° C. In some embodiments, the time sufficient to remove the Boc group from the 2-AA-Boc is from about 1 hour to overnight. In some embodiments, the acid which is incubated with said 2-AA-Boc is neat. In some embodiments, the acid which is incubated with the 2-AA-Boc is in an aprotic, organic solvent. In some embodiments, the aprotic, organic solvent is dimethyl sulfoxide ("DMSO"), dimethyl formamide ("DMF"), or N-methyl formamide. In some embodiments, the aprotic, organic solvent is dimethyl sulfoxide. In some embodiments, the acid is present at a concentration of 1M to 6M. In some embodiments, the acid is DFA and is present at a concentration of about 4M. In some embodiments, the acid is in an aqueous solution and the method further comprises drying the 2-AA after the acid has been incubated with the 2-AA-Boc, to remove the aqueous solution before the 2-AA is incubated with the glycan. In some embodiments, the incubating of the 2-AA with the glycan is at about 50-90° C. In some embodiments, the incubating of the 2-AA with the glycan is at about 65° C. In some embodiments, the solution of the 2-AA and the glycan further comprises a reductant. In some embodiments, the reductant is sodium cyanoborohydride or picoline borane.

In a second group of embodiments, the invention provides kits for labeling glycans with anthranilic acid ("2-AA") by reductive amination. In some embodiments, the kits comprise a container containing 2-AA conjugated to a tert-butyloxycarbonyl ("Boc") group ("2-AA-Boc"), and a container containing an acid suitable for removing the Boc group from the 2-AA-Boc in a concentration sufficient to remove the Boc group from the 2-AA-Boc. In some embodiments, the acid suitable for removing the Boc group is suitable for removing the Boc group under anhydrous conditions. In some embodiments, the acid is trifluoroacetic acid, difluoroacetic acid, or hydrochloric acid. In some embodiments, the acid is difluoroacetic acid. In some embodiments, the difluoroacetic acid is neat. In some embodiments, the acid is in an aprotic, organic solvent. In some embodiments, the aprotic, organic solvent is dimethyl sulfoxide ("DMSO"), dimethyl formamide ("DMF"), or N-methyl formamide. In some embodiments, the aprotic, organic solvent is DMSO. In some embodiments, the acid is present in the aprotic, organic solvent at a concentration of 1M to 6M. In some embodiments, the acid is present in the aprotic, organic solvent at a concentration of about 4M. In some embodiments, the amount of 2-AA-Boc is 5-10 mg. In some embodiments, the kit further comprises a reductant. In some embodiments, the reductant is sodium cyanoborohydride. In some embodiments, the reductant is picoline borane. In some embodiments, the reductant is dissolved in an organic solvent. In some embodiments, the solvent is DMSO.

DETAILED DESCRIPTION

Reductive amination is a common method of labeling glycans for analysis. Two fluorophores, anthranilic acid (2-aminobenzoic acid, or "2-AA") and 2-aminobenzamide, or "2-AB," have been widely used for labeling glycans by reductive amination due to their stability and sensitivity when attached to the glycans. According to the Sigma-Aldrich website, 2-AA is slightly more sensitive for labeling glycans than is 2-AB. Unfortunately, as noted in the Background, the Drug Enforcement Administration ('DEA") has imposed restrictions and record keeping requirements on the use of anthranilic acid, its esters, and its salts because they can also be used in the synthesis of the controlled substance methaqualone. These restrictions have made it harder in the United States to use 2-AA for its legitimate uses in glycan labeling and analysis.

Surprisingly, the invention provides kits and methods of labeling glycans for analysis that allow shipping and use of a derivative of 2-AA that is not anthranilic acid or an ester or salt of anthranilic acid, but which allow introduction and use of the derivative for labeling glycans with only modest modification of standard workflows for such labeling.

The inventive kits and methods employ 2-AA with the amine protected with a tert-butyloxycarbonyl ("Boc") group. Using Boc groups to protect amine groups in organic synthesis is well known in procedures for peptide synthesis. Typically, the Boc protecting group is added, the desired synthesis step is performed, and the protecting group is removed by incubating the compound bearing the Boc group with an acid. Depending on the acid, the incubation may be at ambient temperature, but is preferably at temperatures of 50-90° C. (For convenience of reference, 2-AA to which a Boc group has been covalently attached to what was the amine moiety of the 2-AA molecule will be sometimes be referred to herein as "2-AA-Boc," as "blocked 2-AA," or as "protected 2-AA." Removal of a Boc group from 2-AA-Boc will sometimes be referred to as "deprotecting" the 2-AA or as "unblocking" the 2-AA).

While the use of protection and deprotection of amines is well known in the context of peptide synthesis, it has not been used in the labeling and analysis of glycans in general, or with regard to the use of 2-AA in glycan labeling in particular, as the blocking and unblocking of the 2-AA adds steps and time to the labeling workflow, in direct contrast to the usual desire of practitioners to reduce the number of steps and the time for performing an analysis. It is therefore counterintuitive to block the amine on 2-AA or to use a Boc-protected form of 2-AA. But, here the conjugation of 2-AA to Boc creates a compound that is not 2-AA or an ester or salt of 2-AA and is therefore believed not to be a List 1 chemical. Further, the deprotection step results in 2-AA being present in a mixture with an acid. The combination of the acid with the 2-AA is useful for labeling glycans by reductive amination.

Adding and Removing Boc Protecting Groups

The addition and removal of t-Boc protecting groups has been practiced for decades. See, e.g., Lundt et al., "Removal of t-butyl and t-butoxycarbonyl protecting groups with trifluoroacetic acid," Chem. Biol. & Drug Design, 12(5):258-268 (1978); Atherton et al., J. Chem. Soc., Chem. Commun., 13:537-539 (1978); Hemmasi and Bayer, Int J Pept Protein Res. 9(1):63-70 (1977); Schnolzer et al., "In situ neutralization in Boc-chemistry solid phase peptide synthesis. Rapid, high yield assembly of difficult sequences," Int J Pept Protein Res. 1992 September-October; 40(3-4):180-93; and Han et al., "Fast, efficient and selective deprotection of tert-butoxycarbonyl (Boc) group using HCl/dioxane (4 m)," J. Peptide Res., 58, 338-341 (2001). The addition and removal of Boc protecting groups is taught generally in, for example, Green and Wuts, "Protective Groups in Organic Synthesis, Wiley-Interscience, NY (1999), pp. 518-525 and 736-739.

Boc-protected 2-AA is commercially available from, for example, Sigma Aldrich Corp. (St. Louis, Mo.), which lists it as "2-(Boc-amino)benzoic acid," and Bachem (Bachem Americas, Inc., Torrance, Calif., catalog number A-3240). Alternatively, Boc groups can be added to compounds, such as 2-AA by known techniques. For example, Wikipedia states that a Boc protecting group can be added under "aqueous conditions using di-tert-butyl dicarbonate in the presence of a base such as sodium bicarbonate. Protection of the amine can also be accomplished in acetonitrile solution using 4-dimethylaminopyridine (DMAP) as the base." The article further reports that the Boc group can be removed by using strong acids, such as "trifluoroacetic acid neat or in dichloromethane, or with HCl in methanol." It summarizes various research reports as teaching the deprotection of the protected product with 3 M hydrochloric acid and ethyl acetate for 30 minutes at ambient temperature, heating the protected compound with aqueous hydrochloric acid and toluene at 65° C., and dissolving the protected compound in a 50/50 mix of dichloromethane and trifluoroacetic acid ("TFA").

The Schnolzer reference cited above teaches the rapid removal of Boc protecting groups from amino acids using 100% TFA. As noted above, deprotection protocols typically call for use of a strong acid, such as 3 M hydrochloric acid or trifluoroacetic acid.

Some deprotection schemes known in the art remove the Boc group using acid in an aqueous solution. Aqueous solutions can be used in the inventive methods and kits (an acid in an aqueous solution may sometimes be referred to herein as an "acid aqueous solution"). In these methods, a "drying down" step is used to remove the water after the 2-AA is deprotected, as the subsequent reductive amination of the glycans must be performed under anhydrous conditions. In preferred embodiments, the acid is either neat or is in an aprotic organic solvent, such as dimethyl sulfoxide ("DMSO"), dimethyl formamide ("DMF"), or N-methyl formamide, that is compatible with reductive amination so that it does not have to be removed prior to the labeling of the glycans of interest after the 2-AA is unblocked. Tetrahydrofuran can be used, but is less preferred as it is more volatile. In some preferred embodiments, the organic solvent is DMSO. A mixture of a selected acid and an organic solvent will sometimes be referred to herein as an "acid solution."

Using the acid either neat or in an organic solvent removes the need for a "dry down" step between the deblocking of the 2-AA and the subsequent reductive amination of the glycans using the now-unblocked 2-AA and is therefore preferred. As noted, the acids can be used neat. If an organic solvent is used, the acids are preferably used in a concentration of 1M to 6M, with about 3-5M being more preferred and about 4M even being more preferred, with "about" here meaning ±0.25M.

In preferred embodiments, the 2-AA-Boc is deprotected by incubating it with the acid, acid aqueous solution, or acid solution, for a time and at a temperature sufficient to remove the Boc group from the blocked 2-AA. If the 2-AA-Boc is deprotected in an acid aqueous solution, a "drying down" step is then used to leave the deprotected 2-AA in an anhydrous condition ready for labeling of the glycans.

In some embodiments, the deblocking of the 2-AA and the labeling of the glycans with the 2-AA is performed in the same container (a so-called "one-pot" procedure). This avoids multiple transfers of the reactants to another container, each of which can result in a loss of some of the glycans to be analyzed. For example, the 2-AA-Boc may be mixed with the acid, acid aqueous solution, or acid solution in a vial and the vial then placed in a heating block for a desired period of time, from an hour to overnight. The vial is typically heated to 50-90° C. In some preferred embodiments, the vial is heated to about 70° C., with "about" with regard to temperature meaning ±5° C.

If the 2-AA-Boc has been deprotected using an acid aqueous solution, it is typically then dried down and an organic solvent then added prior to adding the glycans to be labeled. In preferred embodiments, in which 2-AA-Boc has been deprotected by incubation with acid under anhydrous conditions (such as incubation with either neat acid or acid in an aprotic organic solvent) for a time and at a temperature sufficient to remove the Boc group, the glycan sample can be added directly to the anhydrous solution and labeled by the now-unblocked 2-AA by reductive amination. For example, the 2-AA-Boc may be deblocked by incubating it with an acid, such as TFA, in DMSO overnight at a temperature of 70° C., as shown in Scheme 1:

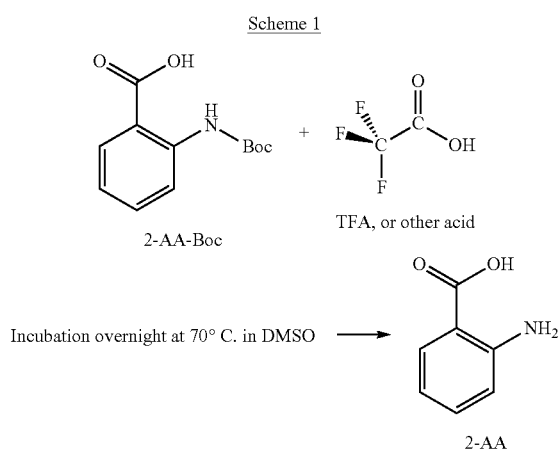

As persons of skill will appreciate, other combinations of incubation times and temperatures for using particular acids to remove Boc groups from protected amino acids are known in the art and may be readily adapted for purposes of removing Boc groups from 2-AA-Boc. As difluoroacetic acid (DFA) is not as strong as acid as is the TFA commonly used in deblocking Boc groups used in peptide synthesis, if DFA is used, the incubation time for deblocking the 2-AA, or the temperature, or both, should be increased modestly over those used in protocols using TFA as the acid to reflect DFA's weaker strength. Any particular time and temperature can be readily tested with any particular concentration of any particular acid in any particular solvent to determine if it results in complete deblocking of the 2-AA-Boc. As 2-AA and 2-AA-Boc are both fluorescent, the resulting products can be readily tested for completeness of the deprotection by, for example, conducting HPLC, examining the fluorescence of the eluted products, and determining the relative amounts of 2-AA and 2-AA-Boc.

A reductant is preferably present during the labeling of the glycans by reductive amination. As use of reductants in such labeling is well known in the art, it will be described only briefly here. Reductants suitable for use in reductive amination of glycans include sodium cyanoborohydride and picoline borane. The reductant is typically in an organic solvent such as DMSO or tetrahydrofuran (THF), but in some workflows, the acid or acid solution may be added to the reductant while it is in solid form, allowing the reductant to then dissolve in the acid or acid solution. The reductant is typically added in a 1:1, 1:2, 1:3, or 1:4 ratio of solution containing the reductant to the solution containing the 2-AA and acid or acid solution. The reductant concentration is typically 0.5 to 2M in the final mixture.

The unblocked 2-AA can be used in normal workflows for reductive amination of glycans of interest. 2-AA is typically used in the labeling of glycans in a concentration of 0.1M to 2M, more preferably in a concentration of 0.3M to 1M, still more preferably in a concentration of about 0.3M to about 0.6M and most preferably in a concentration of about 0.4M, with "about" here meaning 0.05M.

Kits

The invention provides kits comprising 2-AA-Boc and reagents for unblocking the 2-AA-Boc. For example, the kit may provide one or more containers containing an amount of 2-AA-Boc suitable for a selected number of glycan analyses.

For example, glycans may be labeled by 2-AA using a multi-well plate, such as a 96-well plate. Conveniently, the amount of 2-AA-Boc in the container may be chosen so that, when unblocked, the resulting amount of 2-AA will sufficient to label glycan samples in the wells of a 96-well plate. The amount of 2-AA used in labeling glycans is quite small and ~40 mg of 2-AA is typically sufficient to label glycans in all the wells of a 96-well plate. The kits further comprise one or more containers which hold the acid, acid aqueous solution, or acid solvent solution, chosen for use in unblocking the 2-AA-Boc. Conveniently, the container holding the 2-AA-Boc, the container holding the acid, acid aqueous solution, or acid solvent solution, or both the containers, are sized such that once the 2-AA-Boc and the acid or solution comprising the acid have been mixed together, the container holding the resulting mixture can be put into a heating block and incubated at a selected temperature to remove the Boc group, resulting in unblocked 2-AA.

Containers of unblocked 2-AA for labeling typically contain 5-30 mg of an approximately 0.4 M solution of 2-AA. Containers containing the same amount and concentration of 2-AA-Boc, once unblocked, will result in equivalent amounts of 2-AA for labeling.

In preferred embodiments, the kits are not shipped or distributed with containers in which 2-AA-Boc and acid have already been mixed, as that would result in a mixture comprising some unblocked 2-AA along with the acid during distribution and shipping. It is expected that the 2-AA-Boc and the acid will only be mixed together at the site at which labeling and analysis of glycan samples is to be performed and will typically occur just before performing reductive amination of the glycan samples.

The kit may further include a reductant useful in reductive amination with 2-AA. For example, the kit may include as a reductant sodium cyanoborohydride or picoline borane.

The reductant will typically be added to the acid or solution comprising the acid prior to incubation of the acid or acid solution with the 2-AA-Boc.

The kits preferably further include instructions on using the included reagents to provide unblocked 2-AA, including time and temperature conditions for unblocking the 2-AA-Boc using the acid or acid solution provided.

Analyses of Glycans Labeled by 2-AA

Once deprotection of the 2-AA-Boc has occurred, the resulting unblocked 2-AA can be used to label the glycans of interest by standard techniques, such as those described in Abo et al., "Determination of monosaccharides derivatized with 2-aminobenzoic Acid by capillary electrophoresis," Methods Mol Biol. 2013; 984:45-50, Rustighi et al., "Analysis of N-acetylaminosugars by CE: a comparative derivatization study," Electrophoresis. 2009 August; 30(15):2632-9, or Jiang et al., Anal Chim Acta. 2017 Apr. 15; 962:32-40. Conveniently, the glycan or glycans to be analyzed may be added to the receiving vessel containing the now-unblocked 2-AA, and are subjected to reductive amination following standard, well-known protocols to label the glycans, such as those described in the references cited above. Conversely, the now-unblocked 2-AA can be pipetted, poured, or otherwise transferred to a separate container containing the glycans to be labeled, and the reductive amination of the glycans can be performed in the separate container. Optionally, a cleanup step may be performed to remove any excess label. Common methods for cleanup of glycans labeled by reductive amination with 2-AA include hydrophilic interaction liquid chromatography, or "HILIC," or use of graphitized carbon. The labeled glycans can then be analyzed by standard methods, such as those in the references cited above. For example, the labeled glycans may pipetted or eluted from the receiving vessel, subjected to separation by high performance liquid chromatography or capillary electrophoresis, and the presence of labeled glycans detected by observing fluorescence of the separated, labeled glycans.

EXAMPLES

Example 1

This Example sets forth an exemplary workflow for deprotecting 2-AA-Boc and using the resulting deblocked 2-AA in a glycan labeling protocol.

Five mg of 2-AA-Boc powder is placed in a vial, to which is added 0.15 mL of a solution of 4M TFA in DMSO. When the 2-AA-Boc has dissolved in the solution, the vial is placed in a well in a heating block and incubated overnight at 70° C. to remove the Boc group from the 2-AA-Boc, resulting in unblocked 2-AA. The vial is removed from the heating block and allowed to cool before reductant is added in preparation for glycan labeling. 5 µL of the solution containing the newly unblocked 2-AA is pipetted into a vial and 5 µL of a 2M solution of sodium cyanoborohydride in DMSO is added. Dried glycans released from a glycoprotein of interest by enzymatic digestion are then added to the vial and resolubilized in the solution containing the newly unblocked 2-AA and the reductant. The vial may be swirled or vortexed as necessary to see that all of the dried glycans come in contact with the solution and are resolubilized. The vial containing the glycans, now dissolved in the solution, is then placed in a well in a heating block and incubated at 65° C. for three hours, thereby causing reductive amination and labeling of the glycans.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for labeling a glycan with anthranilic acid ("2-AA"), said method comprising (a) obtaining 2-AA conjugated to a tert-butyloxycarbonyl ("Boc") group ("2-AA-Boc"),
   (b) removing said Boc group by incubating said 2-AA-Boc with an acid for a time and at a temperature sufficient to remove said Boc group from said 2-AA-Boc, thereby obtaining 2-AA, and
   (c) incubating a solution containing said 2-AA and said glycan under conditions that allow said 2-AA to label said glycan, thereby labeling said glycan with 2-AA.

2. The method of claim 1, wherein said acid is trifluoroacetic acid, difluoroacetic acid, or hydrochloric acid.

3. The method of claim 1, wherein said temperature sufficient to remove said Boc group from said 2-AA-Boc is 50-90° C.

4. The method of claim 1, wherein said time sufficient to remove said Boc group from said 2-AA-Boc is from about 1 hour to overnight.

5. The method of claim 1, wherein said acid which is incubated with said 2-AA-Boc is neat.

6. The method of claim 1, wherein said acid which is incubated with said 2-AA-Boc is in an aprotic, organic solvent.

7. The method of claim 6, wherein said aprotic, organic solvent is dimethyl sulfoxide ("DMSO"), dimethyl formamide ("DMF"), or N-methyl formamide.

8. The method of claim 1, wherein said acid is present at a concentration of 1M to 6M.

9. The method of claim 1, wherein said acid is in an aqueous solution and said method further comprises step (b'), drying said 2-AA to remove said aqueous solution, between said steps (b) and (c).

10. The method of claim 1, wherein said incubating of step (c) is at about 50-90° C.

11. The method of claim 1, wherein said solution of step (c) further comprises a reductant.

12. The method of claim 11, wherein said reductant is sodium cyanoborohydride or picoline borane.

13. A kit for labeling glycans with anthranilic acid ("2-AA") by reductive amination, said kit comprising (a) a container containing 2-AA conjugated to a tert-butyloxycarbonyl ("Boc") group ("2-AA-Boc"), and (b) a container containing an acid suitable for removing said Boc group from said 2-AA-Boc in a concentration sufficient to remove said Boc group from said 2-AA-Boc.

14. The kit of claim 13, wherein said acid is trifluoroacetic acid, difluoroacetic acid, or hydrochloric acid.

15. The kit of claim 13, wherein said acid is neat or is in an aprotic, organic solvent.

16. The kit of claim 15, wherein said aprotic, organic solvent is dimethyl sulfoxide ("DMSO"), dimethyl formamide ("DMF"), or N-methyl formamide.

17. The kit of claim 15, wherein said acid is present in said aprotic, organic solvent at a concentration of 1M to 6M.

18. The kit of claim 13, further comprising a reductant.

19. The kit of claim 18, wherein said reductant is sodium cyanoborohydride.

20. The kit of claim 18, wherein said reductant is dissolved in an organic solvent.

21. The method of claim 2, wherein said acid is difluoroacetic acid.

22. The method of claim 3, wherein said temperature sufficient to remove said Boc group from said 2-AA-Boc is about 70° C.

23. The method of claim 7, wherein said aprotic, organic solvent is DMSO.

24. The method of claim 8, wherein said acid is difluoroacetic acid and is present at a concentration of about 4M.

25. The method of claim 1, wherein said incubating of step (c) is at about 65° C.

26. The kit of claim 13, wherein said acid suitable for removing said Boc group is suitable for removing said Boc group under anhydrous conditions.

27. The kit of claim 14, wherein said acid is difluoroacetic acid.

28. The kit of claim 13, wherein said acid is in an aprotic, organic solvent.

29. The kit of claim 28, wherein said aprotic, organic solvent is DMSO.

30. The kit of claim 28, wherein said acid is present in said aprotic, organic solvent at a concentration of about 4M.

31. The kit of claim 13, wherein said amount of 2-AA-Boc is 5-10 mg.

32. The kit of claim 18, wherein said reductant is picoline borane.

33. The kit of claim 20, wherein said solvent is DMSO.

* * * * *